US010922945B2

(12) United States Patent
Jungvid et al.

(10) Patent No.: US 10,922,945 B2
(45) Date of Patent: Feb. 16, 2021

(54) BED OR CHAIR EXIT SENSING DEVICE, AND USE OF A BED OR CHAIR EXIT SENSING DEVICE

(71) Applicant: BELLMAN & SYMFON EUROPE AB, Askim (SE)

(72) Inventors: Peter Gustaf Jungvid, Hovås (SE); Peer Gjaerum, Partille (SE); Anders Andersson, Hisings Backa (SE)

(73) Assignee: BELLMAN & SYMFON EUROPE AB, Askim (SE)

( * ) Notice: Subject to any disclaimer, the term of this patent is extended or adjusted under 35 U.S.C. 154(b) by 14 days.

(21) Appl. No.: 16/385,647

(22) Filed: Apr. 16, 2019

(65) Prior Publication Data

US 2019/0340911 A1 Nov. 7, 2019

(30) Foreign Application Priority Data

May 2, 2018 (EP) .................................... 18170437

(51) Int. Cl.
*G08B 21/04* (2006.01)
*G01V 11/00* (2006.01)
*G08B 21/18* (2006.01)

(52) U.S. Cl.
CPC .......... *G08B 21/0461* (2013.01); *G01V 11/00* (2013.01); *G08B 21/182* (2013.01)

(58) Field of Classification Search
CPC ....... A61B 5/1115; A61B 5/11; A61B 5/4809; A61B 5/1116; A61B 5/1118; A61B 5/1114; G08B 21/0461; G08B 21/22
See application file for complete search history.

(56) References Cited

U.S. PATENT DOCUMENTS

2012/0259248 A1* 10/2012 Receveur ............ A61G 7/05792
600/595
2015/0206415 A1* 7/2015 Wegelin .................. G08B 21/22
340/573.4
(Continued)

FOREIGN PATENT DOCUMENTS

| EP | 0778003 A2 * | 6/1997 | .......... A61B 5/1118 |
| EP | 0778003 A2 | 6/1997 | |
| JP | 2013-31770 A | 11/2012 | |

OTHER PUBLICATIONS

European Examination Report issued by the European Patent Office dated Oct. 26, 2018 for corresponding German Application No. 18170437.0, filed May 2, 2018, which the subject application claims priority from.

(Continued)

*Primary Examiner* — Mirza F Alam
(74) *Attorney, Agent, or Firm* — Saliwanchik, Lloyd & Eisenschenk

(57) ABSTRACT

A bed or chair exit sensing device to be placed in, on or in relation to a bed or chair, and adapted to detect a person leaving the bed or chair, comprising a piezoelectric sensor and a data processing device adapted to determine, by processing the signals from the piezoelectric sensor, when the person is leaving the bed, characterized in that the bed or chair exit sensing device comprises an accelerometer sensor, and said data processing device is adapted to determine bed or chair exit of a person on the basis of combined processing of the signal from said piezoelectric sensor and the signal from said accelerometer sensor.

15 Claims, 2 Drawing Sheets

(56) References Cited

U.S. PATENT DOCUMENTS

| | | |
|---|---|---|
| 2016/0025513 A1 | 1/2016 | Bhattacharyya |
| 2016/0157754 A1* | 6/2016 | Shinozuka ............ A61B 5/1115 340/573.7 |
| 2017/0150905 A1* | 6/2017 | Shen ...................... A61B 5/445 |
| 2017/0360357 A1* | 12/2017 | Larson .................. A61B 5/1114 |

OTHER PUBLICATIONS

Hirokazu Madokoro et al. "Unrestrained Multi-Sensor Systems for Real-Time Prediction of Bed-Leaving Behavior Patterns," SICE Annual Conference 2014, Hokkaido University, Sapporo, Japan, Sep. 9-12, 2014.

\* cited by examiner

BED OR CHAIR EXIT SENSING DEVICE, AND USE OF A BED OR CHAIR EXIT SENSING DEVICE

CROSS-REFERENCE TO A RELATED APPLICATION

This application claims priority under 35 U.S.C. 119(e) of European Patent Application No. 18 170 437.0, filed on May 2, 2018, which is incorporated herein by reference in its entirety.

FIELD OF THE INVENTION

The invention relates to a bed or chair exit sensing device to be placed in, on or in relation to a bed or chair, and adapted to detect a person leaving the bed or chair, comprising a piezoelectric sensor and a data processing device adapted to determine, by processing the signals from the piezoelectric sensor, when the person is leaving the bed or chair.

BACKGROUND OF THE INVENTION

EP 0 778 003 A2 discloses a presence detecting apparatus comprising a flexible tape with a piezo-electric element to be fixed on the surface of a bed mattress, and absence and presence judging means for judging absence and presence of a body on the bed on the basis of a signal from the piezo-electric element. The piezo-electric element is connected to a circuit unit, to be arranged for example on the floor and comprising the absence and presence judging means, by a shielded wire, which can be uncomfortable to the user and even dangerous as a source of stumbling.

The problem underlying the present invention is to provide a bed or chair exit sensing device which has a high sensitivity and reliability, a low error rate and is easy and comfortable to handle for the user.

The invention solves this problem with the features of the independent claims. By using an accelerometer sensor as a second independent sensor in addition to the piezo sensor, and determining bed or chair exit of a person on the basis of combined processing of the signal from said piezoelectric sensor and the signal from said accelerometer sensor, two independent sensors are provided (dual sensor technology). This allows a more reliable bed or chair exit determination since complementary information is provided and the result from one sensor can be proved by the result from the other sensor. The use of a piezo sensor ensures a high sensitivity measurement.

Preferably, a bed or chair exit of a person is determined if a condition of a signal from the piezoelectric sensor and a condition of a signal from the accelerometer sensor are fulfilled, in particular within a predetermined period of time. This allows to evaluate the signals from the piezoelectric sensor and from the accelerometer sensor successively, where the combined processing is preferably achieved by proving whether both conditions are met within a predetermined period of time. However, it is possible that a single condition depending on the signals from the piezoelectric sensor and from the accelerometer sensor is evaluated for determining bed or chair exit.

Preferably a first one of said conditions is monitored, and only if the said condition is fulfilled, sampling values from the other sensor (in particular, the piezo sensor) is started in order to determine whether a corresponding second condition is fulfilled. This allows a power saving operation because most of the time, only signals from one of the sensors, for example the accelerometer sensor, are monitored or sampled, while values from the other sensor are sampled only in short time periods following and being triggered by fulfilment of the first condition. This feature is especially advantageous in the case of a fully battery powered sensing device, because it significantly prolongs battery life. Preferably, sampling values from the second sensor is stopped in case the other condition is not fulfilled within the predetermined period of time, which also contributes to saving energy consumption.

Preferably, the data processing device is adapted to determine an inclination angle of the sensing device, and/or a change of the inclination angle over time, from the signal output by the accelerometer sensor. In this case, a bed or chair exit condition can be considered fulfilled if the change of the inclination angle over a predetermined period of time exceeds a first threshold, which is easy to determine and yields a reliable result.

Preferably, a bed or chair exit condition is considered fulfilled if the signal, or the processed signal, from the piezoelectric sensor falls from a high level above a predetermined second threshold, indicating that the person is moving significantly in the monitored bed or chair during getting up, to a low level under a specific third threshold, indicating that the person has left the monitored bed or chair, within a certain period of time.

Expediently the bed or chair exit sensing device comprises a wireless transmitter. In case a bed or chair exit of a person has been determined, the data processing device is adapted to control the wireless transmitter to send out a wireless bed or chair exit signal.

In a preferred embodiment, the bed or chair exit sensing device is battery powered, in particular fully battery powered. The piezoelectric sensor, the data processing device and the accelerometer sensor are preferably arranged inside the same housing of the sensing device. In this embodiment, the sensing device is a self-sustaining single unit, where all electrical components are arranged within the same housing. Due to this feature, the sensing device is compact and there are no disturbing external wire connections.

Preferably the accelerometer sensor provides at least two-dimensional acceleration data in a principal plane of the bed or chair exit sensing device, more preferably three-dimensional acceleration data.

Preferably the wireless transmitter communicates via Bluetooth protocol and/or is part of a Bluetooth mesh.

The inventive sensing device can advantageously be applied to monitoring bed or chair exit of people like elderly, handicapped, dementia patients, epileptics and/or in buildings like hospitals, nursing homes, retirement homes, private homes and the like. A bed is generally a piece of furniture provided for a person to lie on it, and covers all kinds of beds including sofa, chaise longue, couch, divan bed and so on. A chair is generally a piece of furniture provided for a person to sit on it, and covers all kind chairs including arm chair, easy chair, stool, bench, cantilever chair and so on.

Preferably, the bed or chair exit sensing device is adapted to determine also bed or chair entrance, or re-entrance, of a person on the basis of combined processing of the signal from the piezoelectric sensor and the signal from the accelerometer sensor. This can be performed in an analogous manner to the determination of bed or chair exit.

BRIEF DESCRIPTION OF THE FIGURES

In the following the invention shall be illustrated on the basis of preferred embodiments with reference to the accompanying drawings, wherein.

DETAILED DESCRIPTION

Figure 1:
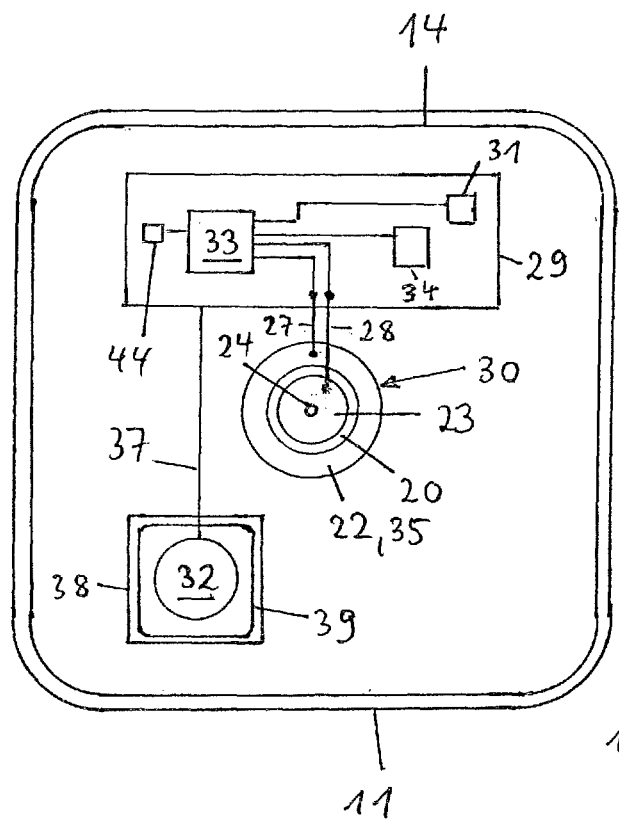
FIG. 1 shows a schematic view on a housing part of a bed or chair exit sensing device.

The bed or chair exit sensing device 13 comprises a housing 10 having housing parts 11, 12 which can be connected to each other to form the housing 10 through connecting elements not shown, for example clips which may be formed integrally with the housing parts 11, 12, screws, or in any other manner, for example by welding. The housing parts 11, 12 contact each other around their respective circumferences, where they are also connected to each other.

In the mounted state, the housing parts 11, 12 enclose a cavity 16 between them where functional elements, to be described later, are preferably arranged. In the mounted state, the housing 10 is preferably flat, i.e. the extension of the housing 10 along a central axis (see FIG. 2) is small, for example at most 20%, of the extension of the housing 10 in the other two directions (see FIG. 1). Due to this feature, the sensing device 13 does not disturb the user when being placed in or on a bed or chair.

The housing parts 11, 12 may be sealed against each other by a circumferential or ring shaped rubber gasket 14. One or both of the housing parts 11, 12 may comprise a circumferential groove to receive the rubber gasket 14. In the mounted state of the housing parts 11, 12, the rubber gasket 14 ensures that the cavity 16 enclosed between the housing parts 11, 12 is sealed against dust and moisture entering from the environment. The housing parts 11, 12, and thus the housing itself, are preferably inflexible or rigid, which distinguishes the sensing device 13 from flexible mats to be placed on a bed mattress. The housing parts 11, 12 may be made of a polymer, in particular a thermoplastic material.

The bed or chair exit sensing device 13 comprises a piezo-electric element 30, or piezo element for short, having a ceramic layer 20, which may have the form of a circular disc, and a metal plate 20 forming a first electrode 35 of the piezo sensor 30. The ceramic layer 20 is preferably coated on the metal plate 22. The metal plate 22, serving as a substrate for the multi-layer piezo sensor 30, may for example be made of brass and be circular as well.

Figure 4:
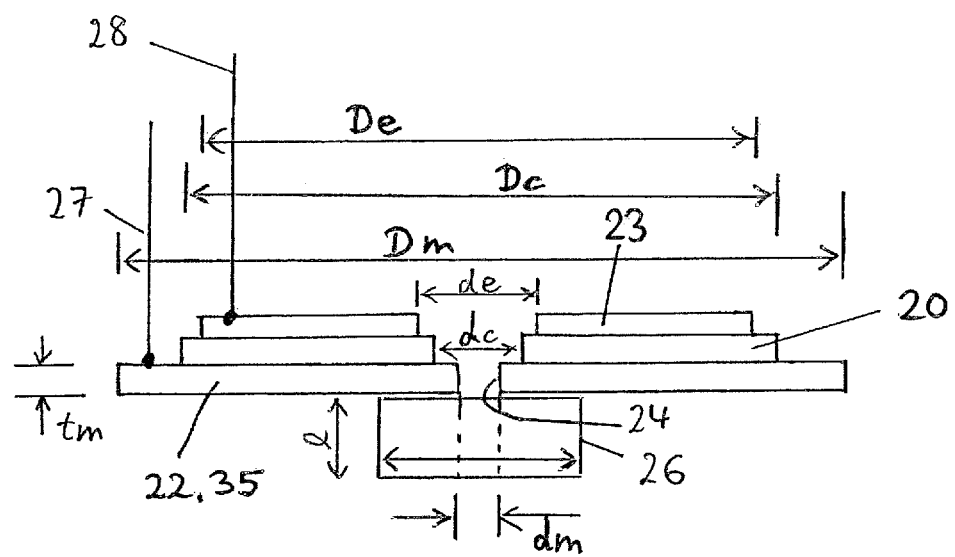
FIG. 4 shows a cross-sectional view of a piezoelectric sensor of a bed or chair exit sensing device.

The outer diameter Dm of the metal plate 22 (see FIG. 4) is preferably at least 20 mm, more preferably at least 25 mm, even more preferably at least 30 mm, for example 35 mm. The inner hole diameter dm of the metal plate 22 is preferably at most 10 mm, more preferably at most 8 mm, even more preferably at most 6 mm, for example 4 mm. The thickness tm of the metal plate 22 is preferably at most 0.5 mm, more preferably at most 0.3 mm and even more preferably at most 0.2 mm, for example 0.1 mm.

The outer diameter Dc of the ceramic layer 20 is preferably at least 10 mm, more preferably at least 15 mm, even more preferably at least 20 mm, for example 25 mm. The outer diameter Dc of the ceramic layer 20 is preferably smaller by at least 10%, more preferably at least 15%, even more preferably at least 20%, most preferably at least 25% than the outer diameter Dm of the metal plate 22, thus leaving a ring-shaped outer part of the metal plate 22 for connecting a lead 27 to the metal plate 22, for example by soldering, and thus to the first electrode.

The inner diameter do of the ceramic layer 22, which is for example in the range between 4.5 mm and 6.5 mm, like 5.5 mm, is preferably larger by at least 5%, more preferably at least 10%, even more preferably at least 15%, most preferably at least 20% than the inner diameter dm of the metal plate 22. Through this feature, the metal plate 22 preferably extending at least 0.5 mm, more preferably at least 1 mm, for example 1.5 mm inwards from the inner edge of the ceramic layer 20, provides a mounting surface for the fastener 25. The diameter of the head of the fastener 25 is preferably smaller than the inner diameter do of the ceramic layer 20, such that the fastener 25 acts or presses on the metal plate 22, only, but not on the ceramic layer 20. In this manner, cracking of the ceramic layer 20 by the fastener 25, which has found to strongly decrease the sensitivity of the piezo element, can be prevented.

On the side opposite the metal plate 22, the ceramic layer 20 preferably comprises an electrically conducting, preferably circular second electrode 23, for example in the form of a Silver coating on the ceramic layer 20. The outer diameter De of the second electrode 23 is preferably at least 10 mm, more preferably at least 15 mm, even more preferably at least 20 mm, for example 23 mm.

The inner diameter de of the second electrode 23, which is for example in the range between 6 mm and 10 mm, like 7 mm, is preferably larger by at least 5%, more preferably at least 10%, even more preferably at least 15%, most preferably at least 20% than the inner diameter do of the ceramic layer 20. Through this feature, the ceramic layer preferably extending at least 0.5 mm, more preferably at least 1 mm, for example 1.5 mm inwards from the inner edge of the second electrode 23, acts as an insulation between the metal plate 22 and the second electrode 23 in order to avoid short circuit. A second lead 28 is connected to the second electrode 23, for example by soldering.

The piezo sensor 30 may have a mounting hole 24 through which a fastener 25 like a screw can extend for mounting the piezo sensor 30 to the housing 10 or one of the housing parts 11. The piezo sensor 30 can be positioned on a mounting base 26 having a significantly smaller diameter than the ceramic layer 20. Through the mounting base 26, the piezo element is mounted to the corresponding housing part 11 with a distance corresponding to the length l or height of the mounting base 26. A mechanical connection between the housing 10 and the piezo sensor 30 is established by the mounting base 26 or, in other embodiments, in any other manner. The mounting hole 24 is preferably in the center, or a central region, of the piezo sensor 30. The mounting base 26 is preferably arranged in the center, or a central area, of the bed or chair exit sensing device 13, as shown in FIG. 1. The mounting base 26 can have the form of a cylinder, or any other suited form. All external impacts on the housing 10 will be transferred via the mounting base 26 to the piezo sensor 30.

The outer diameter Db of the mounting base 26 is preferably small, i.e. less than half of, more preferably less than ⅓ of, even more preferably less than ¼ compared to the outer diameter Dm of the metal plate 22 or the piezo sensor 30. Due to this feature, the metal plate 22 and with it the ceramic layer 22 can vibrate or oscillate freely over a substantial part of it, allowing a sensitive measurement by the piezo sensor 30. I.e., through the mechanical connection between the housing 10 and the piezo sensor 30, and since the fastener 25 fixes the piezo sensor 30 only punctually or in a small area (e.g. less than 10% or less than 5%) as compared to the area of the piezo sensor 30, most of the piezo sensor 30 can freely bend or oscillate under influence of a force acting on the bed or chair exit sensing device 13. The bending or oscillations of the piezo sensor 30 leads to a corresponding electrical signal between the electrodes 23, 35 through piezoelectric effect in the ceramic layer 20. The electrical signal indicating movement of the bed or chair exit sensing device 13 is transmitted from the piezo sensor 30 to the digital processor 33, to be described below, through the leads 27, 28 or in any other manner.

The bed or chair exit sensing device 13 comprises a digital processor 33, like a microcontroller or microprocessor, which is electrically connected to the electrodes 23, 35 of the piezo sensor 30 through the leads 27, 28. In a preferred embodiment, the digital processor 33 is mounted on a printed circuit board 29, to which the leads 27, 28 can be connected for example by soldering. Other electrical connections between the digital processor 33 and the electrodes 23, 35 of the piezo sensor 30 are possible. Analog circuitry, like an amplifier, a filter and/or an A/D converter, can be arranged between the piezo sensor 30 and the digital processor 33.

The bed or chair exit sensing device 13 comprises an accelerometer sensor 34, or accelerometer 34 for short, electrically connected to the digital processor 33. The accelerometer sensor 34 is fixedly mounted to the bed or chair exit sensing device 13 and is preferably adapted to measure the acceleration in three mutually perpendicular directions in space. Therefore, the accelerometer sensor 34 is preferably a tri-axis accelerometer sensor. From the signal output by the accelerometer sensor 34, the digital processor 33 can determine the three-dimensional orientation of the bed or chair exit sensing device 13 in space. In a practical embodiment, the accelerometer sensor 34 may be an electrical component mounted to the printed circuit board 29 also carrying the digital processor 33.

Figure 3:
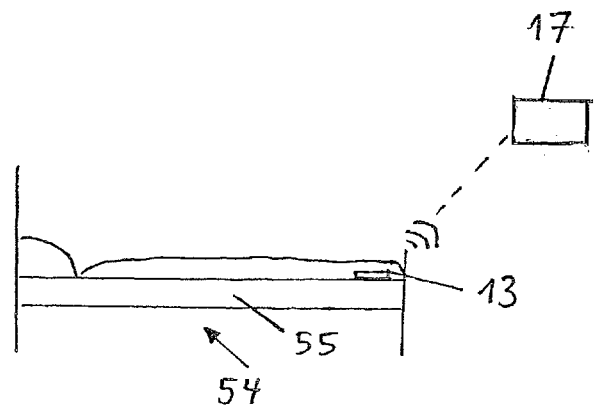
FIG. 3 shows a schematic view for illustrating an application of a bed or chair exit sensing device.

The bed or chair exit sensing device 13 is to be placed in or on a bed 54 or in other mechanical relation to the bed, or to be connected to the bed 54, for example on or under the mattress 55, see FIG. 3. The digital processor 33 is adapted to monitor movement of a person in the bed 54 by combined processing of the signals from the piezo sensor 30 and the accelerometer sensor 34, as will be explained in detail below, and based on evaluation of the person's movement, to determine a time point when the person is leaving the bed. The digital processor 33 can preferably also be adapted to determine a point of time when a person is entering or re-entering the bed 54 based on evaluation of the person's movement.

Furthermore, the bed or chair exit sensing device 13 comprises a wireless transmitter 31, preferably in the form of a wireless transceiver adapted to receive and transmit communication data through wireless communication, and in particular to wirelessly communicate with an external wireless receiver 17. The digital processor 33 is configured to control the wireless transmitter 31 for digital communication. In a practical embodiment, the wireless transmitter 31 may be an electrical component mounted to the printed circuit board 29 also carrying the digital processor 33.

In some applications, the external receiver 17 may be an alerting device adapted to inform a responsible person that a person has left the bed 54 monitored by the bed or chair exit sensing device 13. The external receiver 17 may be a transceiver device adapted to send a wireless signal to a pager or mobile phone of a responsible person. The transceiver device could be wall mounted and/or mains powered, without being restricted to these features. Other applications of the bed or chair exit sensing device 13 and/or the external receiver 17 are possible. The transmitter 31 of the bed or chair exit sensing device 13 and the external receiver 17 preferably communicate with each other via Bluetooth protocol. In a preferred embodiment, the transmitter 31 and the receiver are connected to each other in a Bluetooth Mesh, which allows to extend the range between the transmitter 31 and the receiver 17.

Preferably, the bed or chair exit sensing device 13 is battery powered, i.e., it comprises at least one electric battery 32. This has the advantage that the functioning of the bed or chair exit sensing device 13 does not depend on AC mains supply, and electric wiring between the bed or chair exit sensing device 13 and stationary AC power plugs can be avoided.

Figure 2:
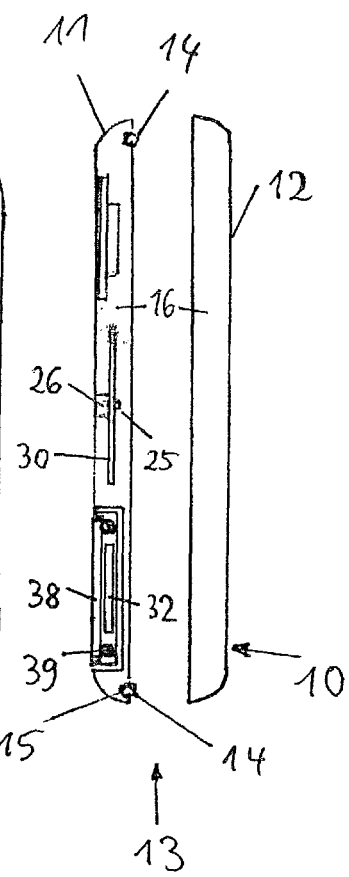
FIG. 2 shows a side view of the housing part of FIG. 1 and a corresponding housing part.

The battery 32 can be arranged on the printed circuit board 29 of the digital processor 33 or, like in FIGS. 1 and 2, separate from it. In the latter case, the battery 32 is electrically connected to the digital processor 33 or the printed circuit board for example by conductors 37. The battery 32 can preferably be replaceable. In order to make the battery 32 accessible, the housing part 11 preferably comprises a removable cover 38 covering a battery compartment where the battery 32 is arranged. The cover 38 may be fixed to the housing part 11 for example by means of a screw or any other suited fastener. The cover 38 is preferably sealed against the housing part 11 by a ring seal 39 for protecting the interior of the housing 10 against dust and moisture.

When the battery 32 is low, i.e. the charge level of the battery 32 falls below a threshold and therefore should be replaced, the bed or chair exit sensing device 13, specifically the digital processor 33, is preferably adapted to send a wireless battery low signal indicating a low level battery via the wireless transmitter 31 to an external device, for example the external receiver 17. The external receiver 17 is adapted to inform the user or service personnel in a suited manner, allowing them to change the battery 32 in the sensing device 13.

The sensing device 13 preferably comprises an optical indicator 44. The optical indicator 44 may comprise one or more LEDs. The optical indicator 44 may have coding, for example color coding, for indicating different states or events of the sensing device 13. The optical indicator 44 may be adapted to indicate that the charge level of the battery 32 is low, for example by color red. The optical indicator 44 may also indicate other events, like start-up or power-up of the sensing device, and/or each time a bed or chair exit has been detected and a bed or chair exit signal has been sent through the wireless transmitter 31.

The optical indicator 44 is preferably arranged on the printed circuit board 29 carrying the digital processor 33, where the material of the housing part 12 towards which the optical indicator 44 is directed is at least semi-transparent such that lighting the optical indicator 44 is perceivable from the outside of the housing 10. It is also possible that the optical indicator 44 is arranged in a receptacle in the housing 10 of the sensing device 13.

In the following, a preferred mode operation of the bed exit sensing device 13 is explained.

When a person is sleeping in the bed 54, the digital processor 33 can preferably be in a low power consumption mode or sleep mode. In the sleep mode, values from the accelerometer 34 are sampled, but values from the piezo sensor 30 are not sampled. This saves power consumption if the monitoring of the accelerometer 34 consumes less energy than the monitoring of the piezo sensor 30. In other words, the digital processor 33 is sleeping while the accelerometer 34 is sampling acceleration data.

When a memory assigned to the accelerometer 34 is full or a predefined quantity of acceleration data have been sampled, the accelerometer 34 wakes up the digital processor 33. The digital processor 33 uses the 3D data from the accelerometer to calculate the actual 3-dimensional angle of orientation of the bed exit sensing device 13 continuously. The resulting tilt data are again processed in an algorithm that outputs the angle change over a period of time.

If the change of the tilt angle of the bed exit sensing device 13 in any direction exceeds a first threshold, the digital processor 33 wakes up, i.e., it goes from the sleep mode to a wake mode, initiates a timer and starts to sample measurement values from the piezo sensor 30 continuously at a defined sampling rate.

The digital processor 33 comprises an algorithm that calculates, and preferably amplifies, changes in the piezo sensor 30 over a period of time. If, as a first condition, a change of the tilt angle of the bed exit sensing device 13 in any direction exceeds a first threshold, and, as a second condition, the output from the piezo sensor 30 changes from a high level exceeding a second threshold, indicating that the person is moving significantly in the monitored bed during getting up, to a low level under a specific third threshold, indicating that the person has left the monitored bed, and both conditions are fulfilled within a certain period of time (i.e., before the timer has exceeded a time threshold), the digital processor 30 determines a bed exit of the person, and triggers and/or sends out a bed exit signal through the wireless transmitter 31. The above evaluation of a first condition of the signal from the accelerometer 34 and of a second condition from the piezo sensor 30 is called combined processing.

However if, after start of sampling of values from the piezo sensor 30, the signal from the piezo sensor 30 continues to be above the specific third threshold during the above mentioned period of time (only first condition fulfilled but not the second condition), the digital processor 33 estimates that the person is still in bed, i.e. he or she moves in the bed without leaving it. Consequently, the digital processor 33 does not determine bed exit of the person in this case and goes back into sleep mode.

Summarizing the above, the digital processor 33, after being woke up by the accelerometer 34, does an analysis on the basis of the accumulated acceleration data, and takes a corresponding decision to either go back to sleep, or to read or sample data from the piezo sensor 30.

Embodiments

Embodiment 1. A bed or chair exit sensing device (13) to be placed in, on or in relation to a bed or chair, and adapted to detect a person leaving the bed or chair, comprising a piezoelectric sensor (30) and a data processing device (33) adapted to determine, by processing the signals from the piezoelectric sensor (30), when the person is leaving the bed or chair, characterized in that the sensing device (13) comprises an accelerometer sensor (34), and said data processing device (33) is adapted to determine bed or chair exit of a person on the basis of combined processing of the signal from said piezoelectric sensor (30) and the signal from said accelerometer sensor (34).

Embodiment 2. The sensing device as claimed in embodiment 1, characterized in that bed or chair exit of a person is determined if a condition of the signal from the piezoelectric sensor (30) and a condition of the signal from the accelerometer sensor (34) are fulfilled.

Embodiment 3. The sensing device as claimed in embodiment 2, characterized in that a first one of said conditions is monitored, and if said first condition is fulfilled, sampling values from the other sensor (30; 34) is started in order to determine whether a corresponding second condition is fulfilled.

Embodiment 4. The sensing device as claimed in embodiment 3, characterized in that said first condition to be monitored is a condition of the signal from the accelerometer sensor (34), and said second condition is a condition of the signal from the piezoelectric sensor (30).

Embodiment 5. The sensing device as claimed in embodiment 3 or embodiment 4, characterized in that sampling values from the other sensor (30; 34) is stopped in case the second other condition is not fulfilled within a predetermined period of time.

Embodiment 6. The sensing device as claimed in any one of the preceding embodiments, characterized in that the data processing device (33) is adapted to determine an inclination angle of the sensing device (13), and/or the change of the inclination angle over time, from the signal output by the accelerometer sensor (34).

Embodiment 7. The sensing device as claimed in embodiment 6, characterized in that a bed or chair exit condition is considered fulfilled if the change of the inclination angle over a predetermined period of time exceeds a first threshold.

Embodiment 8. The sensing device as claimed in any one of the preceding embodiments, characterized in that a bed or chair exit condition is considered fulfilled if the signal from the piezoelectric sensor (30) falls from a level above a second predetermined threshold to below a third predetermined threshold.

Embodiment 9. The sensing device as claimed in any one of the preceding embodiments, characterized in that the bed or chair exit sensing device (13) comprises a wireless transmitter (31), wherein said data processing device (33) is adapted to control said wireless transmitter (31) to send out a wireless bed or chair exit signal in case a bed or chair exit of a person has been determined.

Embodiment 10. The sensing device as claimed in any one of the preceding embodiments, characterized in that the bed or chair exit sensing device (13) is battery powered.

Embodiment 11. The sensing device as claimed in any one of the preceding embodiments, characterized in that the piezoelectric sensor (30), the data processing device (33) and the accelerometer sensor (34) are arranged inside the same housing (10) of the sensing device (13).

Embodiment 12. The sensing device as claimed in embodiments 10 and 11, characterized in that said data processing device (33) is adapted to control said wireless transmitter (31) to send out a battery low signal in case the charge level of at least one battery (32) falls below a threshold.

Embodiment 13. The sensing device as claimed in any one of the preceding embodiments, characterized in that the piezoelectric sensor (30) is mounted on a mounting base (26) with a distance 1 to a housing part (11) of the housing (10).

Embodiment 14. The sensing device as claimed in embodiment 13, characterized in that the outer diameter Db of the mounting base (26) is less than half of the outer diameter Dm of the piezoelectric sensor (30).

Embodiment 15. Use of a sensing device (13) as claimed in any one of the preceding embodiments for detecting a person leaving a bed or chair.

The invention claimed is:

1. A bed or chair exit sensing device, comprising:
   an accelerometer sensor;
   a piezoelectric sensor; and
   a data processing device,
   wherein when the bed or chair exit sensing device is placed in, on, or in related to a bed or chair, said data processing device is adapted to determine a bed or chair exit of a person with respect to the bed or chair on the basis of combined processing of a signal from said accelerometer sensor and a signal from said piezoelectric sensor,
   wherein the bed or chair exit of a person with respect to the bed or chair is determined if a condition of the signal from the accelerometer sensor and a condition of the signal from the piezoelectric sensor are fulfilled,
   wherein a first condition of said condition of the signal from the accelerometer sensor or said condition of the signal from the piezoelectric sensor is monitored, and if said first condition of a corresponding first sensor of the accelerometer sensor or the piezoelectric sensor is fulfilled, sampling values of the signal from the second sensor of the accelerometer sensor and the piezoelectric sensor is started in order to determine whether a corresponding second condition is fulfilled,
   wherein the bed or chair exit sensing device is fully battery powered, and
   wherein the accelerometer sensor, the piezoelectric sensor, and the data processing device are arranged inside a housing of the bed or chair exit sensing device.

2. The sensing device according to claim 1, wherein said first condition to be monitored is the condition of the signal from the accelerometer sensor, and said second condition is the condition of the signal from the piezoelectric sensor.

3. The sensing device according to claim 1, wherein sampling values from the second sensor is stopped in case the second condition is not fulfilled within a predetermined period of time.

4. The sensing device according to claim 2, wherein the data processing device is adapted to determine an inclination angle of the bed or chair exit sensing device, and/or a change of the inclination angle over time, from the signal from the accelerometer sensor.

5. The sensing device according to claim 4, wherein the first condition is considered fulfilled if the change of the inclination angle over a predetermined period of time exceeds a first predetermined threshold.

6. The sensing device according to claim 5, wherein the second condition is considered fulfilled if the signal from the piezoelectric sensor falls from a level above a second predetermined threshold to below a third predetermined threshold.

7. The sensing device according to claim 1, further comprising:
   a wireless transmitter,
   wherein said data processing device is adapted to control said wireless transmitter to send out a wireless bed or chair exit signal in case the bed or chair exit of a person has been determined.

8. The sensing device according to claim 1, wherein said data processing device is adapted to control said wireless transmitter to send out a battery low signal in case a charge level of at least one battery falls below a threshold.

9. The sensing device according to claim 1, wherein piezoelectric sensor is mounted on a mounting base with a distance 1 to a housing part of the housing.

10. The sensing device according to claim 9, wherein an outer diameter Db of the mounting base is less than half of an outer diameter Dm of the piezoelectric sensor.

11. A method for detecting a person exiting a bed or chair, comprising:
    positioning a bed or chair exit sensing device as claimed in claim 1 in, on, or in relation to a bed or chair; and
    processing the signal from the accelerometer sensor and the signal from the piezoelectric sensor, via the data processing device, to determine the bed or chair exit of a person.

12. The method according to claim 11, wherein the bed or chair exit of a person with respect to the bed or chair is determined if a first condition of the signal from the accelerometer sensor and a second condition of the signal from the piezoelectric sensor are fulfilled,
    wherein the first condition of the signal from the accelerometer sensor is monitored, and if said first condition of the accelerometer sensor is fulfilled, sampling values of the signal from the piezoelectric sensor is started in order to determine whether the second condition is fulfilled.

13. The method according to claim 12, wherein the sampling values of the signal from the piezoelectric sensor is stopped in case the second condition is not fulfilled within a predetermined period of time.

14. The method according to claim 13, wherein an inclination angle of the bed or chair exit sensing device, and/or a change of the inclination angle over time, is determined via the data processing device from the signal from the accelerometer sensor,
    wherein the first condition is considered fulfilled if the change of the inclination angle over a predetermined period of time exceeds a first predetermined threshold.

15. The method according to claim 14, wherein the second condition is considered fulfilled if the signal from the piezoelectric sensor falls from a level above a second predetermined threshold to below a third predetermined threshold.

* * * * *